United States Patent

Moses et al.

[11] Patent Number: 6,099,538
[45] Date of Patent: Aug. 8, 2000

[54] SET OF SURGICAL TOOLS AND SURGICAL METHOD FOR CONNECTING SOFT BONE PARTS TO ONE ANOTHER OR TO CONNECTIVE TISSUE

[75] Inventors: Gabriel Moses, Tel Aviv; Ran Oren, Gaaton, both of Israel

[73] Assignee: T.A.G. Medical Products, Kibbutz Gaaton, Israel

[21] Appl. No.: 09/241,429

[22] Filed: Feb. 2, 1999

[51] Int. Cl.⁷ .................................................. A61B 17/04
[52] U.S. Cl. ........................ 606/144; 606/139; 606/148
[58] Field of Search .......................... 606/141, 144–150, 606/139, 180, 163, 184

[56] References Cited

U.S. PATENT DOCUMENTS

| | | | |
|---|---|---|---|
| 919,138 | 4/1909 | Drake et al. | 606/144 |
| 5,520,703 | 5/1996 | Essig et al. | 606/148 |
| 5,709,692 | 1/1998 | Mollenauer et al. | 606/141 |

*Primary Examiner*—Gary Jackson
*Attorney, Agent, or Firm*—Mark M. Friedman

[57] ABSTRACT

Surgical puncture and crochet hooks are provided. Both the puncture and the crochet hooks include (a) a handle; (b) a neck connected to the handle at a proximal end thereof; and (c) a hook element connected to, or integrally formed with, a distal end of the neck. The hook element follows a curved route extending to a side of, and away from, the neck. The hook element of the crochet hook is formed with a distally pointing undercut and a proximally pointing undercut, each of the undercuts is shaped and dimensioned for engaging a surgical suture. Surgical procedures using the puncture and/or crochet hooks are also described.

7 Claims, 3 Drawing Sheets

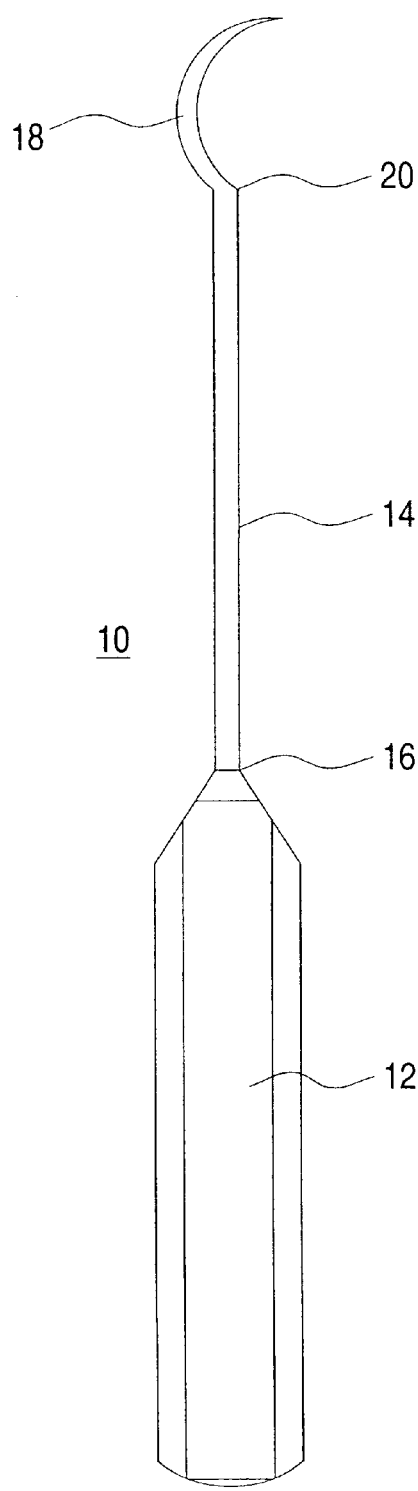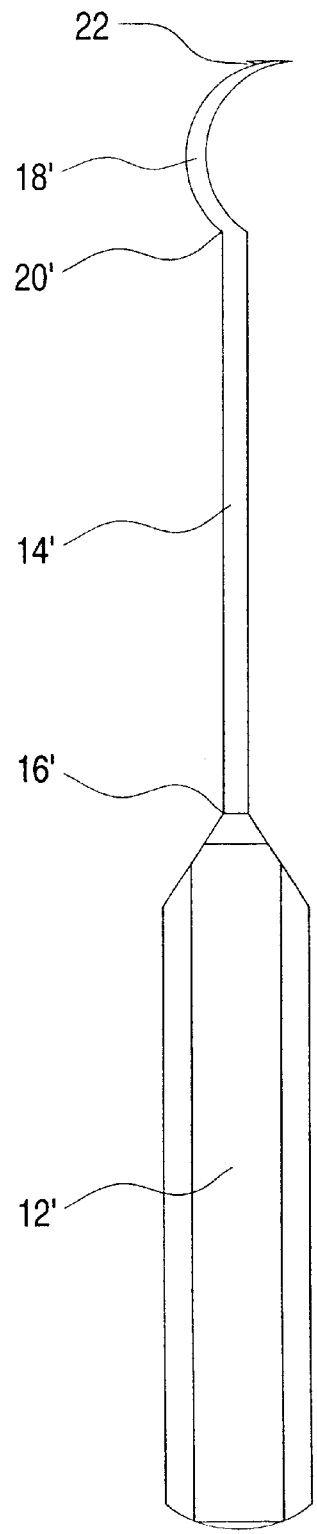
FIG.1
(prior art)
FIG.2
(prior art)

SET OF SURGICAL TOOLS AND SURGICAL METHOD FOR CONNECTING SOFT BONE PARTS TO ONE ANOTHER OR TO CONNECTIVE TISSUE

FIELD AND BACKGROUND OF THE INVENTION

The present invention relates to a set of surgical tools and to a method of using same and, more particularly, to novel punch hook and crochet hook for connecting soft bone parts to one another or to a connective tissue.

A ligament is a band of strong connective tissue serving to connect bones or hold organs in place. A tendon is a cord or band of strong connective tissue serving to connect a muscle with a bone. Both are referred to herein as "connective tissue".

Certain medical conditions are characterized in that a ligament or a tendon detaches or partly detaches from a long bone to which it is operatively connected. In such conditions, it is essential to operatively reconnect the ligament or tendon to the bone from which it has detached.

Other medical conditions are characterized in fractures formed in the terminal, soft parts, of long bones, i.e., at the bone metaphisa or epiphisa portions. In such conditions it is essential to reconnect the fractured bone parts.

Presently, the best mode of reconnecting a detached ligament (or tendon) to its associated long bone or reconnecting fractured soft bone parts is via a suture. One option involves implanting hooks into the bone or fractured bone parts and engaging the suture thereto via the implanted hooks. Another and preferred option involves forming tunnels in the bone or bone parts, through which tunnels the suture is inserted via a crochet hook.

Forming tunnels in the bone or bone parts is effected, according to the prior art, by drilling. This, however, results in loss of bone material and in tunnels of large diameter which weaken the bone or fractured bone parts. In addition, prior art crochet hooks are designed to operate in a single direction, i.e., pulling the suture through the tunnel, however, their design does not permit to push the suture through the channel. This is very limiting especially in cases of minimal invasive operations because, while operated, the crochet hook has to be inserted into the body of the patient through different portals at different stages of the operational procedure to enable the operator to always be able to pull the suture.

There is thus a widely recognized need for, and it would be highly advantageous to have, a punch hook, a crochet hook and a surgical method for connecting soft bone parts to one another or to connective tissue devoid of the above limitations.

SUMMARY OF THE INVENTION

According to one aspect of the present invention there is provided a surgical puncture hook comprising (a) a handle; (b) a neck being connected to the handle at a proximal end thereof; and (c) a hook element being connected to or integrally formed with a distal end of the neck, the hook element following a curved route extending to a side of, and away from, the neck.

According to another aspect of the present invention there is provided a surgical crochet hook comprising (a) a handle; (b) a neck being connected to the handle at a proximal end thereof; and (c) a hook element being connected to or integrally formed with a distal end of the neck, the hook element following a curved route extending to a side of, and away from, the neck, the hook element being formed with a distally pointing undercut and a proximally pointing undercut, each of the undercuts being shaped and dimensioned for engaging a surgical suture.

According to further features in preferred embodiments of the invention described below, the curved route is selected from the group consisting of a left curved route and a right curved route.

According to yet another aspect of the present invention there is provided a surgical method of forming a tunnel in a soft part of a bone, the tunnel being for insertion of a suture therethrough, the method comprising the steps of (a) providing a surgical puncture hook including (i) a handle; (ii) a neck being connected to the handle at a proximal end thereof; and (iii) a hook element being connected to or integrally formed with a distal end of the neck, the hook element following a curved route extending to a side of, and away from, the neck; and (b) using the surgical puncture hook to form the tunnel in the soft part of the bone.

According to still another aspect of the present invention there is provided a surgical method of inserting a suture in a tunnel formed in a bone, the method comprising the steps of (a) providing a surgical crochet hook including (i) a handle; (ii) a neck being connected to the handle at a proximal end thereof; and (iii) a hook element being connected to or integrally formed with a distal end of the neck, the hook element following a curved route extending to a side of, and away from, the neck, the hook element being formed with a distally pointing undercut and a proximally pointing undercut, each of the undercuts being shaped and dimensioned for engaging a surgical suture; (b) engaging the suture at the proximally pointing undercut; and (c) pushing the hook element through the tunnel, so as to push the suture through the tunnel, thereby inserting the suture through the tunnel.

According to an additional aspect of the present invention there is provided a surgical method of forming a tunnel in a soft part of a bone and inserting a suture through the tunnel, the method comprising the steps of (a) providing a surgical puncture hook including (i) a first handle; (ii) a first neck being connected to the first handle at a proximal end thereof; and (iii) a first hook element being connected to or integrally formed with a distal end of the first neck, the first hook element following a curved route extending to a side of, and away from, the first neck; and (b) using the surgical puncture hook to form the tunnel in the soft part of the bone; (c) providing a surgical crochet hook including (i) a second handle; (ii) a second neck being connected to the second handle at a proximal end thereof; and (iii) a second hook element being connected to or integrally formed with a distal end of the second neck, the second hook element following a curved route extending to a side of, and away from, the second neck, the second hook element being formed with a distally pointing undercut and a proximally pointing undercut, each of the undercuts being shaped and dimensioned for engaging a surgical suture; (d) engaging the suture at the proximally pointing undercut; and (e) pushing the hook element through the tunnel, so as to push the suture through the tunnel, thereby inserting the suture through the tunnel.

The present invention successfully addresses the shortcomings of the presently known configurations by providing surgical puncture and crochet hooks and surgical method of employing same for allowing minimal invasive operations to be performed in cases where open surgeries are typically performed.

BRIEF DESCRIPTION OF THE DRAWINGS

The invention herein described, by way of example only, with reference to the accompanying drawings, wherein:

FIG. 1 is a side view of a prior art puncture hook;

FIG. 2 is a side view of a prior art crochet hook;

DESCRIPTION OF THE PREFERRED EMBODIMENTS

Figure 3A:
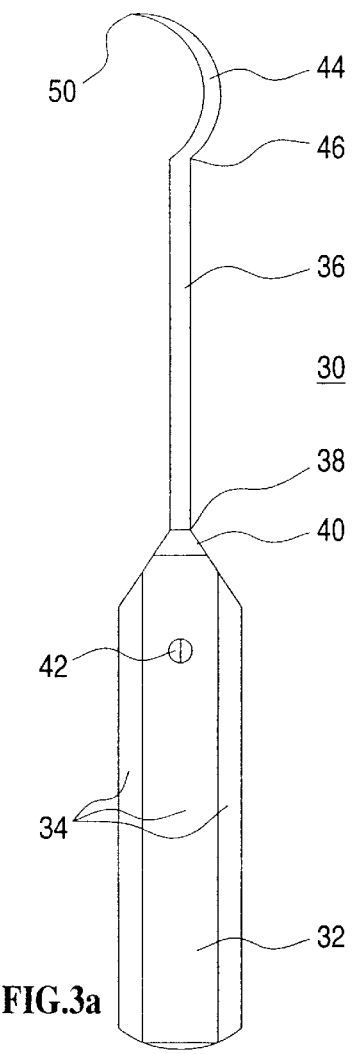
FIGS. 3a–b are side and top (distal end) views of a puncture hook according to the present invention.

The present invention is of novel punch hook and crochet hook which can be used, as a set, for connecting soft bone parts to one another or to a connective tissue. Specifically, the present invention can be used for connecting a worn (partly detached) or torn (fully detached) rotator cuff to the humerus proxima.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 4A:
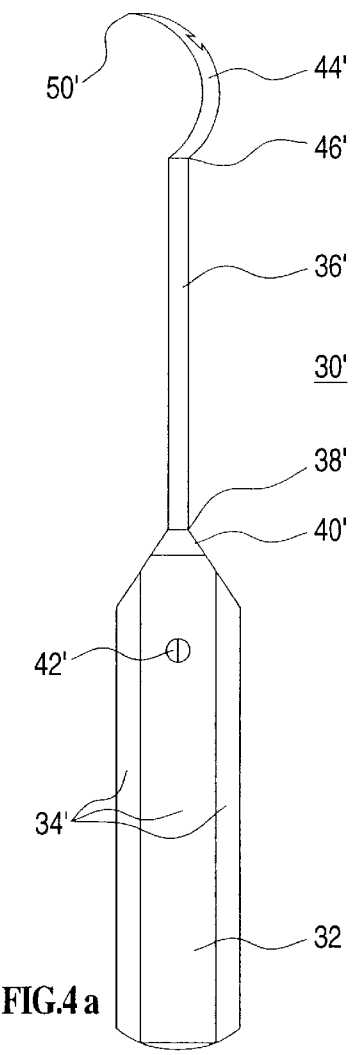
FIGS. 4a–b are side and top (distal end) views of a prior art crochet hook according to the present invention.
Figure 4B:
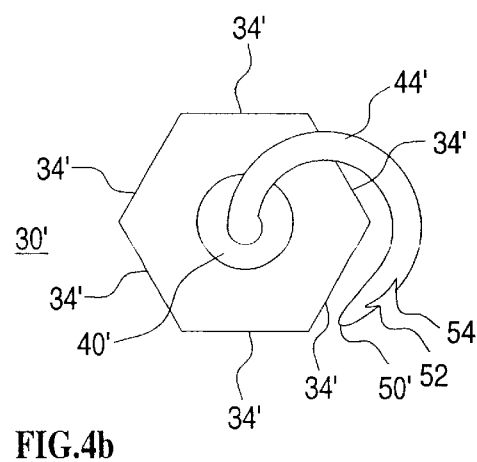
Figure 5:
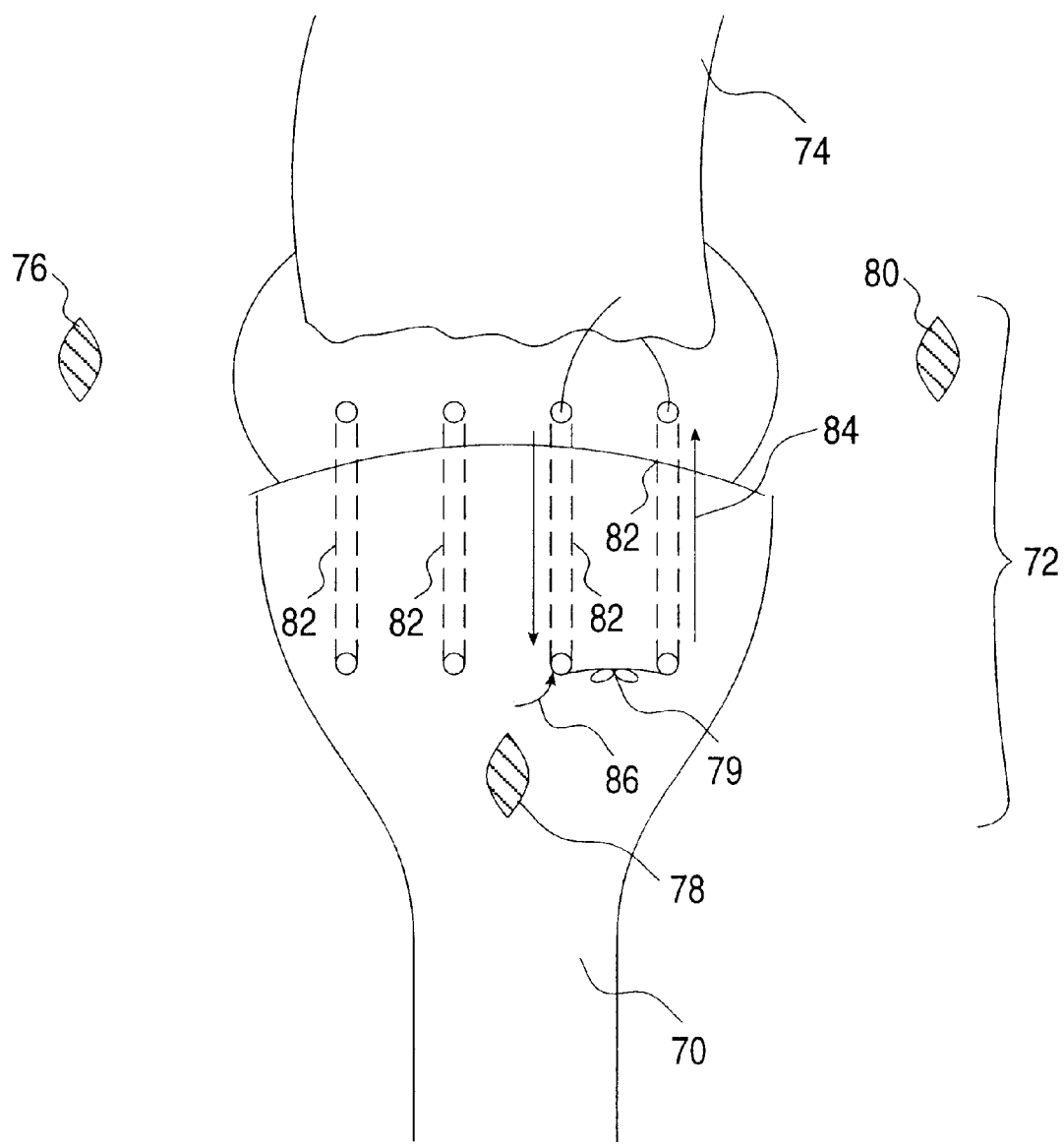
FIG. 5 is a schematic depiction of a surgical procedure for rotator cuff repairing according to the present invention.

For purposes of better understanding the present invention, as illustrated in FIGS. 3–5 of the drawings, reference is first made to the construction and operation of conventional (i.e., prior art) puncture and crochet hooks as illustrated in FIGS. 1–2, respectively.

Thus, as shown in FIG. 1, a prior art puncture hook 10 includes a handle 12 and a neck 14 connected to handle 12 at a proximal end 16 of neck 14. Puncture hook 10 further includes a hook element 18. Hook element 18 is connected to, or integrally formed with, a distal end 20 of neck 14. Hook element 18 follows a curved route which forms a part of a plane defined by neck 14. The orientation of hook element 18 with respect to neck 14 is limiting because in order to puncture a tissue using puncture hook 10, the surgeon, while holding handle 12, is required to bend his hand wrist in a downward/upward motion which is both inconvenient and inaccurate. It is therefore not surprising that such prior art puncture hooks are not used for puncturing tunnels in soft parts of bones.

As shown in FIG. 2, a prior art crochet hook 10' includes a handle 12' and a neck 14' connected to handle 12' at a proximal end 16' of neck 14'. Puncture hook 10' further includes a hook element 18'. Hook element 18' is connected to, or integrally formed with, a distal end 20' of neck 14'. Hook element 18' follows a curved route which forms a part of a plane defined by neck 14'. Hook element 18' is formed with a distally pointing undercut 22 shaped and dimensioned for engaging a surgical suture. Such a construction is limiting in that, while it is effective in pulling a suture, it fails to permit pushing the suture, because while doing so, the suture slips out of undercut 22.

Figure 3B:
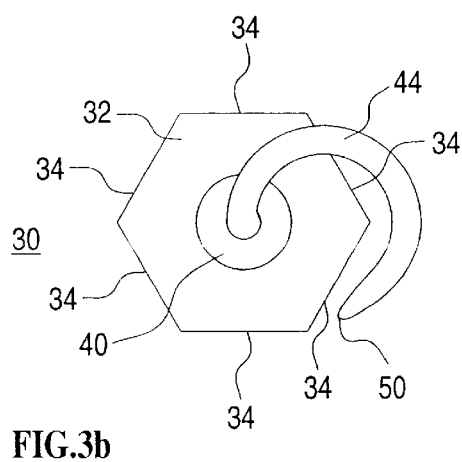

FIGS. 3a–b illustrate a surgical puncture hook according to the present invention, which is referred to hereinbelow as puncture hook 30.

Puncture hook 30 includes a handle 32. Handle 32 is formed conveniently hand-held and operated. To this end, handle 32 preferably include a plurality of faces 34, and/or finger accepting grooves. Handle 32 is preferably made of an autoclavable material such as heat resistant plastic or metal, and it preferably features a rough surface, so as to prevent slippage.

Puncture hook 30 further includes a neck 36. Neck 36 is connected to handle 32 at a proximal end 38 of neck 36. Connecting neck 36 to handle 32 can be effected via a plurality of alternatives. According to one alternative, handle 32 is provided in two halves, each is formed with a central longitudinal groove, such that when the halves are brought together, neck 36 tightly fits into the longitudinal tunnel formed by the joined grooves. According to another alternative, handle 32 is provided with an internal bore which opens at handle's 32 distal end 40, the bore serves for tightly accommodating neck 36. In both cases, however, a screw 42 can be used to secure neck 36 to handle 32.

Puncture hook 30 further includes a hook element 44. Hook element 44 is connected to, or integrally formed with, a distal end 46 of neck 36. In sharp contrast with prior art hook element 18, which is shown in FIG. 1, hook element 44, as best seen in the top (distal end) view of FIG. 3b, follows a curved route extending to a side of, and away from, neck 36. Thus, in contrast with the prior art, hook element 44 does not form a part of a plane defined by neck 36.

Hook element 44 of puncture hook 30 according to the present invention is preferably formed with a pointed, sharp, end 50, so as to enable efficient puncturing of soft bone tissue.

The orientation of hook element 44 with respect to neck 36 is advantageous over the prior art because in order to puncture a tissue using puncture hook 30, the surgeon, while holding handle 32, is required to swivel his hand wrist in a right/left swiveling motion which is much more convenient and accurate as compared with a downward/upward motion. In turn, puncture hook 30 according to the present invention can be readily used to puncture tunnels in soft parts of bones, either in invasive or in minimal invasive (e.g., arthroscopy) surgical procedures.

FIGS. 4a–b illustrate a surgical crochet hook according to the present invention, which is referred to hereinbelow as crochet hook 30'.

Crochet hook 30' includes a handle 32'. Handle 32' is formed conveniently hand-held and operated. To this end, handle 32' preferably include a plurality of faces 34', and/or finger accepting grooves. Handle 32' is preferably made of an autoclavable material such as heat resistant plastic or metal, and it preferably features a rough surface, so as to prevent slippage.

Crochet hook 30' further includes a neck 36'. Neck 36' is connected to handle 32' at a proximal end 38' of neck 36'. Connecting neck 36' to handle 32' can be effected by a plurality of alternatives. According to one alternative, handle 32' is provided in two halves, each formed with a central longitudinal groove, such that when the halves are brought together, neck 36' tightly fits into the longitudinal tunnel formed by the joined grooves.

According to another alternative, handle 32' is provided with an internal bore which opens at handle's 32' distal end 40', the bore serves for tightly accommodating neck 36'. In both cases, however, a screw 42' can be used to secure neck 36' to handle 32'.

Crochet hook 30' further includes a hook element 44'. Hook element 44' is connected to, or integrally formed with, a distal end 46 of neck 36'. In sharp contrast with the prior art hook element 18', which is shown in FIG. 2, hook element 44', as best seen in the top view of FIG. 4b, follows a curved route extending to a side of, and away from, neck 36'. Thus, in contrast with the prior art, hook element 44' does not form a part of a plane defined by neck 36'.

Hook element 44' of crochet hook 30' according to the present invention is preferably formed with a rounded or blunt end 50', so as to avoid causing damage to tissues while operated.

The orientation of hook element 44' with respect to neck 36' is advantageous over the prior art because in order to operate hook 30' the surgeon, while holding handle 32' is required to swivel his hand wrist in a right/left swiveling motion which is much more convenient and accurate as compared with a downward/upward motion.

Hook element 44' of crochet hook 30' according to the present invention is further distinctive and advantageous over the prior art, as further detailed hereinafter.

Thus, hook element 44' of crochet hook 30' according to the present invention is formed with a distally pointing undercut 52 and a proximally pointing undercut 54. Each of undercuts 52 and 54 is shaped and dimensioned for engaging a surgical suture. According to a preferred embodiment, distally pointing undercut 52 is located distally (closer to end 50') to proximally pointing undercut 54, however, the reverse configuration is also envisaged. According to another preferred embodiment undercuts 52 and 54 are integrated so as to form a single groove featuring two undercut ends. The latter configuration is specifically shown in FIGS. 4a–b.

The design of crochet hook 30' allows the surgeon to pull a suture while engaged by, and within, distally pointing undercut 52. However, in sharp distinction from the prior art crochet hook shown in FIG. 2, the design of crochet hook 30' according to the present invention further allows the surgeon to pull a suture while engaged by, and within, proximally pointing undercut 54. As further detailed hereinunder, this feature of crochet hook 30' has advantages in operations in which inserting a suture through a tunnel formed in a bone is exercised.

According to preferred embodiments of the present invention, puncture hooks 30 and crochet hooks 30' are provided as a surgical set. Such a set preferably includes puncture hooks 30 and crochet hooks 30' wherein the curved route is either left handed or right handed. Such a set preferably includes puncture hooks 30 and crochet hooks 30' having hook elements 44 or 44' following curved routes of different diameters. Preferred diameters are 19 mm and 24 mm. Thus, according to a preferred embodiment of the present invention, a surgical set includes eight pieces: four puncture hooks 30, two of a larger diameter and two of a smaller diameter, two left handed and two right handed; and four crochet hooks 30', two of a larger diameter and two of a smaller diameter, two left handed and two right handed.

According to another aspect of the present invention there is provided a surgical method of forming a tunnel in a soft part of a bone. The tunnel can serve for insertion of a suture therethrough. The method according to this aspect of the present invention is effected by using surgical puncture hook 30 according to any of the above described configurations to form a tunnel in the soft part of the bone. This is effected by first positioning end 50 of hook element 44 against the tissue and then, by swiveling the hand wrist, inserting hook element 44 into the tissue, so as to form a tunnel therein. As a result, tissue is compressed sideways, however, substantially no tissue loss is experienced. In addition tunnel formation can readily be effected employing a minimal invasive procedure, such as arthroscopy. The method according to this aspect of the present invention can be used to form tunnels in metaphisa and epiphisa portions of the long bones of the body, such as, but not limited to, the femur, the tibia and the humerus.

According to yet another aspect of the present invention there is provided a surgical method of inserting a suture in a tunnel formed in a bone. The method is effected by engaging the suture at proximally pointing undercut 54 of hook element 44' of crochet hook 30' according to any of the above described configurations thereof and pushing hook element 44' through the tunnel, so as to push the suture through the tunnel, thereby inserting the suture through the tunnel.

The surgical tools according to the present invention can be used to reconnect soft bone parts to one another or to a connective tissue, i.e., ligaments or tendons.

The following sections describe a surgical procedure known as "humerus cuff repair" in which the humerus rotator cuff (connective tissue) is reconnected to the humerus proxima (soft bone tissue) following tear or wear. The procedure is described herein using arthroscopy, however, a similar procedure can be performed using an open joint surgery.

FIG. 5 shows a humerus bone 70, the proxima thereof 72 is formed of a soft bone, and a detached rotator cuff 74, which is normally connected to humerus proxima 72.

FIG. 5 further shows three portals formed in the body of the patient, a posterior portal 76 which serves for positioning an arthroscope equipped with an illumination channel and further with a wash water line, a lateral portal 78 and an arterial portal 80, through the latter suction is applied.

The puncture hook according to the present invention is introduced into the shoulder joint via lateral portal 78 and is used to puncture two or more (four are shown) tunnels 82 in humerus proxima 72. The puncture hook is then removed from the joint.

Then, a suture is engaged in the proximally pointing undercut of the crochet hook according to the present invention. The crochet hook and the suture are thereafter introduced into the joint via lateral portal 78 and the hook element of the crochet hook is used to push the suture through one of tunnels 82, as indicated in FIG. 5 by arrow 84.

A surgical grasper, which is introduced into the joint via portal 80, is used to grasp and demount the suture, while the crochet hook is retracted. Aided by a suture passer (a device designed to pass a suture through connective tissues), which is also introduced into the joint via portal 80, the surgeon passes the suture through rotator cuff 74. At this point, the crochet hook is reintroduced into the joint via portal 78 and its hook element is inserted, as indicated by arrow 86, through one end an adjacent tunnel 82, so as to have the tip thereof extending through the other end of that tunnel 82. A grasper, introduced via portal 80 is then used to engage the suture onto the distally pointing undercut of the hook element of the crochet hook. The crochet hook is then retracted to thereby pull the suture through the adjacent tunnel. A pair of graspers introduced via portal 78 are then used to pull the two free ends of the suture and to form a knot 79 therebetween, to thereby reconnect rotator cuff 74 to humerus proxima 72. In a similar fashion additional pairs or channels can be formed in humerus proxima 72 for inserting an additional suture therethrough in an exact manner.

It will be appreciated by one ordinarily skilled in the art that many similar procedures can be used to otherwise achieve similar reconnection results. However, common features to all of these similar procedures include (i) the use of a puncture hook to form tunnels; and (ii) the use of a crochet hook formed with proximally and distally pointing undercuts to enable both pushing and pulling a suture through the tunnels.

These two features were experimentally found to be very advantageous because (i) the tunnels formed in the bone are narrow and are not associated with bone loss and debris formation, which is a main characteristic of bone drilling procedures; and (ii) the procedure is shortened by about 30 minutes.

The surgical tools according to the present invention can be similarly used to reconnect ligaments or tendons which detach from the bone to which they are normally attached. Thus, the tools and method according to the present invention can be used to reconnect, for example, the anterior cruciate ligament to the tibia; and the lateral collateral ligament or the medial collateral ligament to the femur and/or the tibia, because the above listed ligaments are known to detach directly from the bone to which they are normally connected.

Similarly, the surgical tools according to the present invention can be used to connect fractured soft bone parts. In this case tunnels are formed in both parts of the fractured bone via the puncture hook according to the present invention and a suture or sutures are inserted therein by the crochet hook according to the present invention by pulling or pushing, depending on the specific needs. Candidate soft bones, include, but are not limited to, the proxima humerus, the tibial tuberosity, the greater trochater, the distal radius and the calcaneus.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A surgical puncture hook comprising:
   (a) a handle;
   (b) a neck being connected to said handle at a proximal end thereof; and
   (c) a solid hook element being connected to or integrally formed with a distal end of said neck, said solid hook element following a curved route extending to a side of, and away from, said neck and accomplishing less than a full turn, said solid hook element being shaped and being of sufficient structural rigidity so as to enable puncturing a bone tissue.

2. The surgical puncture hook of claim 1, wherein said curved route is selected from the group consisting of a left curved route and a right curved route.

3. A surgical crochet hook comprising:
   (a) a handle;
   (b) a neck being connected to said handle at a proximal end thereof; and
   (c) a hook element being connected to or integrally formed with a distal end of said neck, said hook element following a curved route extending to a side of, and away from, said neck, said hook element being formed with a distally pointing undercut and a proximally pointing undercut, each of said undercuts being shaped and dimensioned for engaging a surgical suture.

4. The surgical crochet hook of claim 3, wherein said curved route is selected from the group consisting of a left curved route and a right curved route.

5. A surgical method of forming a tunnel in a soft part of a bone, said tunnel being for insertion of a suture therethrough, the method comprising the steps of:
   (a) providing a surgical puncture hook including:
      (i) a handle;
      (ii) a neck being connected to said handle at a proximal end thereof; and
      (iii) a hook element being connected to or integrally formed with a distal end of said neck, said hook element following a curved route extending to a side of, and away from, said neck; and
   (b) using said surgical puncture hook to form the tunnel in the soft part of the bone.

6. A surgical method of inserting a suture in a tunnel formed in a bone, the method comprising the steps of:
   (a) providing a surgical crochet hook including:
      (i) a handle;
      (ii) a neck being connected to said handle at a proximal end thereof; and
      (iii) a hook element being connected to or integrally formed with a distal end of said neck, said hook element following a curved route extending to a side of, and away from, said neck, said hook element being formed with a distally pointing undercut and a proximally pointing undercut, each of said undercuts being shaped and dimensioned for engaging a surgical suture;
   (b) engaging the suture at said proximally pointing undercut; and
   (c) pushing said hook element through the tunnel, so as to push the suture through the tunnel, thereby inserting the suture through the tunnel.

7. A surgical method of forming a tunnel in a soft part of a bone and inserting a suture through the tunnel, the method comprising the steps of:
   (a) providing a surgical puncture hook including:
      (i) a first handle;
      (ii) a first neck being connected to said first handle at a proximal end thereof; and
      (iii) a first hook element being connected to or integrally formed with a distal end of said first neck, said first hook element following a curved route extending to a side of, and away from, said first neck; and
   (b) using said surgical puncture hook to form the tunnel in the soft part of the bone;
   (c) providing a surgical crochet hook including:
      (i) a second handle;
      (ii) a second neck being connected to said second handle at a proximal end thereof; and
      (iii) a second hook element being connected to or integrally formed with a distal end of said second neck, said second hook element following a curved route extending to a side of, and away from, said second neck, said second hook element being formed with a distally pointing undercut and a proximally pointing undercut, each of said undercuts being shaped and dimensioned for engaging a surgical suture;
   (d) engaging the suture at said proximally pointing undercut; and
   (e) pushing said hook element through the tunnel, so as to push the suture through the tunnel, thereby inserting the suture through the tunnel.

* * * * *